(12) United States Patent
Agarwal et al.

(10) Patent No.: US 7,932,039 B2
(45) Date of Patent: *Apr. 26, 2011

(54) NUCLEIC ACID DETECTION ASSAYS EMPLOYING BLOCKER OLIGONUCLEOTIDES

(75) Inventors: Poonam Agarwal, Madison, WI (US); Robert W. Kwiatkowski, Jr., Hopewell Junction, NY (US)

(73) Assignee: Third Wave Technologies, Inc., Madison, WI (US)

( * ) Notice: Subject to any disclaimer, the term of this patent is extended or adjusted under 35 U.S.C. 154(b) by 86 days.

This patent is subject to a terminal disclaimer.

(21) Appl. No.: 12/360,819

(22) Filed: Jan. 27, 2009

(65) Prior Publication Data

US 2009/0203018 A1    Aug. 13, 2009

Related U.S. Application Data

(63) Continuation of application No. 11/592,458, filed on Nov. 3, 2006, now Pat. No. 7,482,127.

(60) Provisional application No. 60/733,335, filed on Nov. 3, 2005.

(51) Int. Cl.
*C12Q 1/68*    (2006.01)
*C07H 21/02*    (2006.01)
*C07H 21/04*    (2006.01)

(52) U.S. Cl. ........................ 435/6; 536/23.1; 536/24.3

(58) Field of Classification Search ..... 435/6; 536/23.1, 536/24.3

See application file for complete search history.

(56) References Cited

U.S. PATENT DOCUMENTS

| | | | |
|---|---|---|---|
| 5,001,050 A | 3/1991 | Blanco | |
| 5,198,543 A | 3/1993 | Blanco | |
| 5,614,402 A | 3/1997 | Dahlberg | |
| 5,795,763 A | 8/1998 | Dahlberg | |
| 5,843,669 A | 12/1998 | Kaiser | |
| 5,846,717 A | 12/1998 | Brow | |
| 5,985,557 A | 11/1999 | Prudent | |
| 5,994,069 A | 11/1999 | Hall | |
| 6,001,567 A | 12/1999 | Brow | |
| 6,001,983 A | 12/1999 | Benner | |
| 6,090,543 A | 7/2000 | Prudent | |
| 6,090,606 A | 7/2000 | Kaiser | |
| 6,117,634 A | 9/2000 | Langmore | |
| 6,183,960 B1 | 2/2001 | Lizardi | |
| 6,194,149 B1 | 2/2001 | Neri | |
| 6,197,557 B1 | 3/2001 | Makarov | |
| 6,210,884 B1 | 4/2001 | Lizardi | |
| 6,235,502 B1 | 5/2001 | Weissman | |
| 6,291,187 B1 | 9/2001 | Kingsmore | |
| 6,323,009 B1 | 11/2001 | Lasken | |
| 6,528,254 B1 | 3/2003 | Sorge | |
| 6,589,743 B2 | 7/2003 | Sorge | |
| 6,627,159 B1 | 9/2003 | Bedingham | |
| 6,692,917 B2 | 2/2004 | Neri | |
| 6,720,187 B2 | 4/2004 | Bedingham | |
| 6,734,401 B2 | 5/2004 | Bedingham | |
| 6,814,935 B2 | 11/2004 | Harms | |
| 6,872,816 B1 | 3/2005 | Hall | |
| 6,875,572 B2 | 4/2005 | Prudent | |
| 6,913,881 B1 | 7/2005 | Aizenstein | |
| 7,026,168 B2 | 4/2006 | Bedingham | |
| 7,045,289 B2 | 5/2006 | Allawi | |
| 7,060,436 B2 | 6/2006 | Lyamichev | |
| 7,122,364 B1 | 10/2006 | Lyamichev | |
| 7,150,982 B2 | 12/2006 | Allawi | |
| 7,189,508 B2 | 3/2007 | Sorge | |
| 7,195,871 B2 | 3/2007 | Lyamichev | |
| 7,256,020 B2 | 8/2007 | Lyamichev | |
| 7,303,869 B2 | 12/2007 | Stevens | |
| 7,482,127 B2 * | 1/2009 | Agarwal et al. .................. 435/6 |

FOREIGN PATENT DOCUMENTS

| | | |
|---|---|---|
| WO | WO97/27214 | 7/1997 |
| WO | WO98/23774 | 6/1998 |
| WO | WO98/39485 | 9/1998 |
| WO | WO98/42873 | 10/1998 |
| WO | WO98/050403 | 11/1998 |
| WO | WO01/88190 | 11/2001 |
| WO | WO01/90337 | 11/2001 |
| WO | WO01/98537 | 12/2001 |
| WO | WO02/00934 | 1/2002 |
| WO | WO02/070755 | 9/2002 |
| WO | WO03/073067 | 9/2003 |

OTHER PUBLICATIONS

Els et al., An invasive cleavage assay for direct quantitation of specific RNAs. Nature Biotechnology 19 : 673-676 (2001).*
Ledford et al., a Multi-Site Study for Detection of the Factor V (Leiden) Mutation from Genomic DNA Using a Homogeneous Invader Microtiter Plate Fluorescence Resonance Energy Transfer (FRET) Assay. Journal of Molecular Diagnostics 2(2) : 97-104 (2000).*
Lyamichev, et al., "Experimental and theoretical analysis of the invasive signal amplification reaction" Biochemistry 39:9523-9532 (2000).
Allawi, et al. "Thermodynamics and NMR of internal G.T mismatches in DNA" Biochemistry. Aug. 26, 1997;36 (34):10581-94.
Anderson, et al. "Quantitative Filter Hybridization" Nucleic Acid Hybridization (1985) Chapter 4, pp. 73-111.
Doty, et al. "Strand Separation and Specific Recombination in Deoxyribonucleic Acids: Physical Chemical Studies" Proc Natl Acad Sci U S A. Apr. 1960;46(4):461-76.
Hall, et al. "Sensitive detection of DNA polymorphisms by the serial invasive signal amplification reaction" Proc Natl Acad Sci U S A. Jul. 18, 2000;97(15):8272-7.
Kong, et al. "Synthesis and duplex stability of oligonucleotides containing cytosine-thymine analogues" Nucleic Acids Res. vol. 17pp. 10373-10383, (1989).

(Continued)

*Primary Examiner* — Ethan Whisenant
(74) *Attorney, Agent, or Firm* — Casimir Jones, S.C.

(57) ABSTRACT

The present invention provides methods, compositions, and kits for detecting the presence or absence of target sequences in a sample, where the sample also contains interfering sequences that are similar or identical to the target sequences. In particular, the present invention provides blocker oligonucleotides that at least partially inhibit the formation of invasive cleavage structures with the interfering sequences but do not substantially inhibit the formation of invasive cleavage structures with the target sequences.

18 Claims, 6 Drawing Sheets

OTHER PUBLICATIONS

Kong, et al. "Synthesis of oligodeoxyribonucleotides containing degenerate bases and their use as primers in the polymerase chain reaction" Nucl. Acid. Res. vol. 20 pp. 5149-5152, (1992).

Lennard, et al., "Genetic variation in response to 6-mercaptopurine for childhood acute lymphoblastic leukaemia" Lancet, 336:225-229, 1990.

Lyamichev, et al. "Polymorphism identification and quantitative detection of genomic DNA by invasive cleavage of oligonucleotide probes" Nat Biotechnol. Mar. 1999;17(3):292-6.

Marmur, et al. "Strand Separation and Specific Recombination in Deoxyribonucleic Acids: Biological Studies" Proc Natl Acad Sci U S A. Apr. 1960;46(4):453-61.

Reynaldo, et al. "The kinetics of oligonucleotide replacements" J Mol Biol. Mar. 24, 2000 vol. 297(2) pp. 511-520.

Schweitzer, et al. "Aromatic Nonpolar Nucleosides as Hydrophobic Isoteres of Pyrimidine and Purine Nucleosides" J. Org. Chem., 1994, 59, 7238-7242.

Schweitzer, et al. "Hydrophobic, Non-Hydrogen-Bonding Bases and Base Pairs in DNA" J. Am. Chem. Soc., 1995, 117, 1863-1872.

Selvin "Fluorescence resonance energy transfer" Methods Enzymol. 1995;246:300-34.

Stryer "Fluorescence energy transfer as a spectroscopic ruler" Annu Rev Biochem. 1978;47:819-46.

Tyagi, et al. "Wavelength-shifting molecular beacons" Nat Biotechnol. Nov. 2000;18(11):1191-6.

* cited by examiner

*3B – INVADER Assay Without Blocker on Genomic DNAs

*3B-INVADER Assay without Blocker on Synthetic Targets

Figure 5

```
           Probe Footprint            INVADER oligo Footprint
SEQ ID NO:1
5' atttgacatgatttgggatagaggagcattagttgcattaatccaggtgatcgcaaatggtaagtaattttcttttttgttagctgtct 3' TPMT SEQ ID NO:2
5' atttgacatgatttgggatagaggagcattagttgcattaatccaggtgatcgcaaatgctatgcggatataatgttatccctcctgggaaa 3' Ch18 974-Z5
                                        3' ccactagcgttacgatacgcctatattacaataggaggacc 5' 974-Z5
                                         3' ggtccactagcgtttacgatacgcctatattacaataggaggacc 5' 1319-Z1
                                        3' cggtaattaggtccactagcgtttacgatacgcctatattacaataggaggacc 5' 1319-Z3
```

Predicted Tm

INVADER Oligo—

5' catttgcgatcacctggattaatggcaactaatga 3' (SEQ ID NO:6)              75°C         • INVADER assay with out
                                                                                    blocker oligo.

Blocker to displace INVADER oligo—

Blocker 1 (974-Z5) (SEQ ID NO:3)
5' ccaggagggataacattatatccgcatagcatttgcgatcacc                       79°C         • Blocker oligos designed to
                                                                                    displace the 5' end of the
Blocker 2 (1319-Z1) (SEQ ID NO:4)                                                   INVADER oligo but only on
5' ccaggagggataacattatatccgcatagcatttgcgatcacctgg                    80.8°C        chromosome 18.

Blocker 3 (1319-Z3) (SEQ ID NO:5)
5' ccaggagggataacattatatccgcatagcatttgcgatcacctgattaatggc            82°C

INVADER oligo Tm after Displacement—                                           • INVADER oligo in the
                                                                                    presence of blocker oligo is
5' tggattaatggcaactaatg (portion left after blocker 1) (SEQ:7)       58.5°C        not stable on chromosome 18
5' attaatggcaactaatg    (portion left after blocker 2) (SEQ:8)       50.8°C        at reaction temperature (63
5'       caactaatg      (portion left after blocker 3) (SEQ:9)       19°C          degree C).

SEQUENCE LISTING

```
<160> NUMBER OF SEQ ID NOS: 22

<210> SEQ ID NO 1
<211> LENGTH: 93
<212> TYPE: DNA
<213> ORGANISM: Artificial Sequence
<220> FEATURE:
<223> OTHER INFORMATION: Synthetic

<400> SEQUENCE: 1
atttgacatg atttgggata gaggagcatt agttgccatt aatccaggtg atcgcaaatg      60
gtaagtaatt tttctttttt tgtttagctg tct                                   93

<210> SEQ ID NO 2
<211> LENGTH: 93
<212> TYPE: DNA
<213> ORGANISM: Artificial Sequence
<220> FEATURE:
<223> OTHER INFORMATION: Synthetic

<400> SEQUENCE: 2
atttgacatg atttgggata gaggagcatt agttgccatt aatccaggtg atcgcaaatg      60
ctatgcggat ataatgttat ccctcctggg aaa                                   93

<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
ccaggaggga taacattata tccgcatagc atttgcgatc acc                        43
```

-continued

```
<210> SEQ ID NO 4
<211> LENGTH: 46
<212> TYPE: DNA
<213> ORGANISM: Artificial Sequence
<220> FEATURE:
<223> OTHER INFORMATION: Synthetic

<400> SEQUENCE: 4
ccaggaggga taacattata tccgcatagc atttgcgatc acctgg         46

<210> SEQ ID NO 5
<211> LENGTH: 55
<212> TYPE: DNA
<213> ORGANISM: Artificial Sequence
<220> FEATURE:
<223> OTHER INFORMATION: Synthetic

<400> SEQUENCE: 5
ccaggaggga taacattata tccgcatagc atttgcgatc acctggatta atggc    55

<210> SEQ ID NO 6
<211> LENGTH: 35
<212> TYPE: DNA
<213> ORGANISM: Artificial Sequence
<220> FEATURE:
<223> OTHER INFORMATION: Synthetic

<400> SEQUENCE: 6
catttgcgat cacctggatt aatggcaact aatga                    35

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tggattaatg gcaactaatg                                      20

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
attaatggca actaatg                                         17

<210> SEQ ID NO 9
<211> LENGTH: 9
<212> TYPE: DNA
<213> ORGANISM: Artificial Sequence
<220> FEATURE:
<223> OTHER INFORMATION: Synthetic

<400> SEQUENCE: 9 caactaatg                                                   9

<210> SEQ ID NO 10
<211> LENGTH: 31
<212> TYPE: DNA
<213> ORGANISM: Artificial Sequence
<220> FEATURE:
<223> OTHER INFORMATION: Synthetic
```

-continued

<400> SEQUENCE: 10
acggacgcgg agctcctcta tcccaaatca t                          31

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
cgcgccgagg ttcctctatc ccaaatcatg                            30

<210> SEQ ID NO 12
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at this position is linked to a Z28
      quenching group.

<400> SEQUENCE: 12
tctaagccgg ttttccggct gagactccgc gtccgt                     36

<210> SEQ ID NO 13
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at this position is linked to a Z28
      quenching group.

<400> SEQUENCE: 13
tctaagccgg ttttccggct gagacctcgg cgcg                       34

<210> SEQ ID NO 14
<211> LENGTH: 57
<212> TYPE: DNA
<213> ORGANISM: Artificial Sequence
<220> FEATURE:
<223> OTHER INFORMATION: Synthetic

<400> SEQUENCE: 14
aacatgtcag tgtgatttta ttttatctat gtctcattta cttttctgta agtagaa    57

<210> SEQ ID NO 15
<211> LENGTH: 31
<212> TYPE: DNA
<213> ORGANISM: Artificial Sequence
<220> FEATURE:
<223> OTHER INFORMATION: Synthetic

<400> SEQUENCE: 15
cgcgccgagg tataactttt caaaaagaca g                          31

<210> SEQ ID NO 16
<211> LENGTH: 36
<212> TYPE: DNA
<213> ORGANISM: Artificial Sequence
<220> FEATURE:

<223> OTHER INFORMATION: Synthetic

<400> SEQUENCE: 16
atgacgtggc agaccataac ttttcaaaaa gacagt                                    36

<210> SEQ ID NO 17
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at this position is linked to a Z28
      quenching group.

<400> SEQUENCE: 17
tctaagccgg ttttccggct gagacctcgg cgcg                                      34

<210> SEQ ID NO 18
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at this position is linked to a Z28
      quenching group.

<400> SEQUENCE: 18
tctttcggcc ttttggccga gagagtctgc cacgtcat                                  38

<210> SEQ ID NO 19
<211> LENGTH: 61
<212> TYPE: DNA
<213> ORGANISM: Artificial Sequence
<220> FEATURE:
<223> OTHER INFORMATION: Synthetic

<400> SEQUENCE: 19
cctctattta gtcatttgaa aacataattt aagtgtaaat gtatgatttt atgcaggttt          60
t                                                                          61

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
agctcgtccg acagcagacc ggggac                                               26

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
cgcgccgagg ccagaccggg gacac                                                25

<210> SEQ ID NO 22

```
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at this position is linked to a Z28
      quenching group.

<400> SEQUENCE: 22
tctttcggcc ttttggccga gagatgtcgg acgagct                              37
```

NUCLEIC ACID DETECTION ASSAYS EMPLOYING BLOCKER OLIGONUCLEOTIDES

This application is a continuation of application Ser. No. 11/592,458, filed on Nov. 3, 2006, which issued as U.S. Pat. No. 7,482,127 on Jan. 27, 2009, and which claims priority to U.S. Provisional Application Ser. No. 60/733,335, filed Nov. 3, 2005, each of which is incorporated herein by reference.

FIELD OF THE INVENTION

The present invention relates to methods, compositions, and kits for detecting the presence or absence of target sequences in a sample, where the sample also contains interfering sequences that are similar or identical to the target sequences. In particular, the present invention provides blocker oligonucleotides that at least partially inhibit the formation of cleavage structures with the interfering sequences but do not substantially inhibit the formation of cleavage structures with the target sequences.

BACKGROUND OF THE INVENTION

Thiopurine S-Methyltransferase (TPMT) catalyzes thiopurine S-methylation, an important metabolic pathway for drugs such as 6-mercaptopurine (6-MP). 6-MP acts as a thiopurine antimetabolite, and is commonly used in the therapy of acute lymphoblastic leukemia (ALL), ulcerative colitis and Chron's disease, inflammatory bowel disease, and other diseases. 6-MP can be acted upon by several metabolic routes, one of which generates 6-Thioguanine nucleotides (6-TGN), the antimetabolite responsible for 6-MP's therapeutic effects. An alternative metabolic route involves the S-methylation of 6-MP, which leads to its inactivation. This led to studies of a correlation between TPMT activity levels and response to 6-MP therapy (see Lennard et al., Lancet, 336:225-229, 1990, herein incorporated by reference). The results of this study showed that children with lower 6-TGN concentrations had higher TPMT activities and a higher subsequent relapse rate, indicating that genetically determined TPMT activity may be an important regulator of the cytotoxic effect of 6-MP.

The most common allele for TPMT deficiency is designated TMPT*3A, which consists of 2 SNPs, G460A and A719G, both of which lead to amino acid changes in the TPMT enzyme. While both mutations together cause a complete loss of activity of the TPMT enzyme, the G460A mutation, when alone, causes a 9-fold reduction in TPMT enzymatic activity. The G460A mutation, in the absence of the second polymorphism A719G, is designated TPMT*3B.

While the TPMT gene is located on chromosome 6p22.3, a highly homologous TPMT pseudogene is located on chromosome 18. Due to the high sequence similarity of the two genes, detection assays designed to interrogate base 460 may be compromised due to interference caused by the presence of the pseudogene. This type of interference may be present when attempting to interrogate other polymorphic sequences present in the genome of a given organism with detection assays. As such, what is needed are methods and compositions for use with detection assays, particularly hybridization based detection assay that minimize or eliminate the interference that can be caused by interfering sequences.

SUMMARY OF THE INVENTION

The present invention provides methods, compositions, and kits for detecting the presence or absence of target sequences in a sample, where the sample also contains interfering sequences that are similar or identical to the target sequences. In particular, the present invention provides blocker oligonucleotides that at least partially inhibit the formation of cleavage structures with the interfering sequences but do not substantially inhibit the formation of cleavage structures with the target sequences. The present invention is illustrated with invasive cleavage assays. However, the present invention is not limited to such embodiments.

In some embodiments, the present invention provides methods of detecting the presence of absence of a target sequence in a sample comprising; a) providing; i) first nucleic acid molecules and second nucleic acid molecules, wherein the first and second nucleic acid molecules are configured to form a first invasive cleavage structure with a target sequence, and wherein the first and second nucleic acid molecules are also able to form a second invasive cleavage structure with an interfering sequence, ii) a sample comprising: A) a target region suspected of containing the target sequence, and B) an interfering region comprising the interfering sequence, iii) a cleavage agent, and iv) blocker oligonucleotides configured to at least partially hybridize with the interfering region such that formation of the second invasive cleavage structure is at least partially inhibited (e.g. 30%, 40%, 50%, 70%, 80%, 90, 95%, 98% or 100% inhibited); b) contacting the sample with the first and second nucleic acid molecules, the cleavage agent, and the blocker oligonucleotides, and c) detecting the presence or absence of the target sequence in the sample. The first and second nucleic acid molecules may, for example, be pre-synthesized or may be generated during the reaction (e.g., by primer extension).

In particular embodiments, the detecting comprises observing a signal generated by cleavage of the first nucleic acid molecules, wherein at least 70 percent (or at least 80, 85, 90, 92, 94, 96, 98, 99, or 100 percent) of the signal results from cleavage of the first nucleic acid molecules in the first invasive cleavage structure. In other embodiments, the contacting is conducted under conditions such that the first nucleic acid molecules hybridize about equally to the target and the interfering sequences. In some embodiments, the first nucleic acid molecules when hybridized to the target sequence have a first Tm, and wherein the first nucleic acid molecules when hybridized to the interfering sequence have a second Tm that is substantially the same as the first Tm (e.g. within 1, 2, or 3° C.), and wherein during the contacting step, the blocker oligonucleotides do not cause any difference between the first and second Tm's to substantially change (e.g. the difference in Tm's changes by 0.3° C. or less). In particular embodiments, the Tm of the second nucleic acid molecules with regard to the interfering region during the contacting step is less than 63° C. (e.g. as a result of the presence of the blocker oligonucleotides). In particular embodiments, the contacting is conducted in the presence of INVADER assay reagents.

In certain embodiments, the present invention provides kits for detecting the presence or absence of a target sequence in a sample comprising; a) first nucleic acid molecules and second nucleic acid molecules, wherein the first and second nucleic acid molecules are configured to form a first invasive cleavage structure with a target sequence, and wherein the first and second nucleic acid molecules are also able to form a second invasive cleavage structure with an interfering sequence, and b) blocker oligonucleotides configured to at least partially hybridize with the interfering region such that formation of the second invasive cleavage structure is at least partially inhibited (e.g. 30%, 40%, 50%, 70%, 80%, 90, 95%, 98% or 100% inhibited). In some embodiments, the kit further comprises; c) a cleavage agent, wherein the cleavage agent is capable of cleaving the first nucleic acid molecules when invasive cleavage structures are formed.

In additional embodiments, the present invention provides compositions comprising; a) first and second nucleic acid molecules, wherein the first and second nucleic acid molecules are configured to form a first invasive cleavage structure with a target sequence, and wherein the first and second nucleic acid molecules are also able to form a second invasive cleavage structure with an interfering sequence, and b) blocker oligonucleotides configured to at least partially hybridize with the interfering region such that formation of the second invasive cleavage structure is at least partially inhibited (e.g. 30%, 40%, 50%, 70%, 80%, 90, 95%, 98% or 100% inhibited).

In certain embodiments, the melting temperature of the blocker oligonucleotides when hybridized to the interfering sequence is greater (higher) than the melting temperature of the second nucleic acid molecules when hybridized to the interfering sequence. In other embodiments, the blocker oligonucleotides are configured to hybridize to at least a portion of the interfering region. In some embodiments, the blocker oligonucleotides are configured to hybridize to at least a portion of the interfering sequence and to at least a portion of the interfering region that is not part of the interfering sequence. In additional embodiments, the blocker oligonucleotides do not substantially alter the ability of the first nucleic acid molecules to hybridize to the target and interfering sequences.

In certain embodiments, the first nucleic acid molecules comprise a 5' portion and a 3' portion, wherein the 3' portion is configured to hybridize to the target sequence, and wherein the 5' portion is configured to not hybridize to the target sequence. In other embodiments, the second nucleic acid molecules comprises a 5' portion and a 3' portion, wherein the 5' portion is configured to hybridize to the target sequence, and wherein the 3' portion is configured to not hybridize to the target sequence.

In some embodiments, the interfering sequence (e.g., which is located in an interfering region) is identical to the target sequence (e.g., which is located in a target region). In other embodiments, the interfering sequence is at least 94 percent (or 95, 96, 97, 98 or 99 percent) homologous to the target sequence. In particular embodiments, the interfering sequence has five or less nucleotide base differences compared to the target sequence. In other embodiments, the target sequence and the interfering sequence are each at least 15 bases in length (e.g. 15-60 bases, 17-50 bases, etc.). In certain embodiments, the target region comprises a first gene, and wherein the interfering region comprises a first pseudo-gene. In other embodiments, the first gene is an allele of the TPMT gene selected from the wild-type allele and a mutant allele (e.g., TPMT *3B (G460A)).

In certain embodiments, the target sequence comprises a targeted polymorphic sequence. In additional embodiments, the targeted polymorphic sequence is a single nucleotide polymorphism. In particular embodiments, the cleavage agent is capable of cleaving the first nucleic acid molecules when the invasive cleavage structures are formed.

In some embodiments, the present invention provides methods of detecting the presence or absence of a TPMT allele in a sample comprising; a) contacting the sample with first and second nucleic acid molecules, wherein the first and second nucleic acid molecules are configured to form an invasive cleavage structure with a target sequence, wherein the target sequence comprises a TPMT allele, and b) detecting the presence or absence of the target sequence in the sample.

In particular embodiments, the present invention provides methods for detecting at least one TPMT allele in a sample, comprising using a first and a second nucleic acid molecules, wherein the first and second nucleic acid molecules are configured to form an invasive cleavage structure with a target sequence comprising the at least one TPMT allele.

In certain embodiments, the TPMT allele is selected from the group consisting of wild-type, *3B (G460A), *3C (A719G), and *2 (G238C). In further embodiments, the detecting comprises observing a signal generated by cleavage of the first nucleic acid molecules, thereby identifying the presence of the TPMT allele in the sample.

In additional embodiments, the present invention provides methods of detecting the presence of absence of a target sequence comprising; a) providing; i) probe nucleic acid molecules configured to hybridize to a target sequence, wherein the probe nucleic acid molecules are also able to hybridize to identical interfering sequences; ii) a sample comprising: A) a target region suspected of containing the target sequence, and B) an interfering region comprising the interfering sequence; iii) a cleavage agent capable of cleaving the probe nucleic acid molecules when hybridized to the target and interfering sequences, and iv) blocker oligonucleotides configured to at least partially hybridize with the interfering region, b) contacting the sample with the probe nucleic acid molecules and blocker oligonucleotides under conditions such that the blocker oligonucleotides at least partially reduce the efficiency of cleavage of probe nucleic acid molecules when hybridized to the interfering sequence; and c) detecting the presence or absence of the target sequence in the sample. In particular embodiments, the contacting is conducted in the presence of INVADER assay reagents. In particular embodiments, the detecting comprises observing a signal generated by cleavage of the probe nucleic acid molecules, wherein at least 70 percent (or at least 80, 85, 90, or 95 percent) of the signal results from cleavage of the probe nucleic acid molecules when hybridized to the target sequence.

In some embodiments, the present invention provides methods for screening candidate blocker oligonucleotides comprising; a) providing; i) first and second nucleic acid molecules, wherein the first and second nucleic acid molecules are configured to form a first invasive cleavage structure with a target sequence, and wherein the first and second nucleic acid molecules are also able to form a second invasive cleavage structure with an interfering sequence, ii) a sample comprising: A) a target region containing the target sequence, and B) an interfering region comprising the interfering sequence, iii) a cleavage agent, and iv) a candidate blocker oligonucleotide configured to at least partially hybridize with the interfering region; b) contacting a first portion of the sample with the first and second nucleic acid molecules, the cleavage agent, and without the candidate blocker oligonucleotide, and contacting a second portion of the sample with the first and second nucleic acid molecules, the cleavage agent, and the candidate blocker oligonucleotide, and c) comparing the signal generated from the first portion of the sample to the signal generated from the second portion of the sample in order to determine if the candidate blocker oligonucleotide reduces the signal from the second portion of the sample (e.g., where a reduced signal indicates that the candidate blocker oligonucleotide at least partially inhibits the formation of the second invasive cleavage structure).

DEFINITIONS

To facilitate an understanding of the present invention, a number of terms and phrases are defined below:

As used herein, the term "INVADER assay reagents" refers to one or more reagents for detecting target sequences, said reagents comprising nucleic acid molecules capable of forming an invasive cleavage structure in the presence of the target sequence. In some embodiments, the INVADER assay reagents further comprise an agent for detecting the presence of an invasive cleavage structure (e.g., a cleavage agent). In some embodiments, the nucleic acid molecules comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. INVADER assay reagents may be found, for example, in U.S. Pat. Nos. 5,846,717; 5,985,557; 5,994,069; 6,001,567; 6,913,881; and 6,090,543, WO 97/27214, WO 98/42873, Lyamichev et al., Nat. Biotech., 17:292 (1999), Hall et al., PNAS, USA, 97:8272 (2000), each of which is herein incorporated by reference in their entirety for all purposes.

In some embodiments, INVADER assay reagents are configured to detect a target nucleic acid sequence comprising first and second non-contiguous single-stranded regions separated by an intervening region comprising a double-stranded region. In certain embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., Mn2+ and/or Mg2+ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (including but not limited to a reaction tube or a well, as in, e.g., a microtiter plate). In certain preferred embodiments, the INVADER assay reagents are provided in microfluidic devices such as those described in U.S. Pat. Nos. 6,627,159; 6,720,187; 6,734,401; and 6,814,935, as well as U.S. Pat. Pub. 2002/0064885, all of which are herein incorporated by reference. In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, software (e.g., for collecting and analyzing data), inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes; radiolabels such as 32P; binding moieties such as biotin; haptens such as digoxygenin; luminogenic, phosphorescent or fluorogenic moieties; mass tags; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246:300, each incorporated herein by reference). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In preferred embodiments, the emission spectrum of the acceptor dye is distinct from the emission spectrum of the donor dye such that emissions from the dyes can be differentiated (e.g., spectrally resolved) from each other.

In some embodiments, a donor dye is used in combination with multiple acceptor moieties. In a preferred embodiment, a donor dye is used in combination with a non-fluorescing quencher and with an acceptor dye, such that when the donor dye is close to the quencher, its excitation is transferred to the quencher rather than the acceptor dye, and when the quencher is removed (e.g., by cleavage of a probe), donor dye excitation is transferred to an acceptor dye. In particularly preferred embodiments, emission from the acceptor dye is detected. See, e.g., Tyagi, et al., Nature Biotechnology 18:1191 (2000), which is incorporated herein by reference.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "Tm" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation: Tm=81.5+0.41(% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of Tm.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides, or longer. The exact size will depend on many factors, which in turn depend on the ultimate function or use of the oligonucleotide. The oligonucleotide may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "invasive cleavage structure" as used herein, refers to a structure that is formed by the interaction of at least one probe oligonucleotide and a target nucleic acid, forming a structure comprising a duplex, the resulting structure being cleavable by a cleavage agent, including but not limited to an enzyme. The cleavage structure is a substrate for specific cleavage by the cleavage agent in contrast to a nucleic acid molecule that is a substrate for non-specific cleavage by agents such as phosphodiesterases which cleave nucleic acid molecules without regard to secondary structure (i.e., no formation of a duplexed structure is required). One example of an invasive cleavage structure is shown in FIG. 1A.

The term "cleavage agent" as used herein refers to any agent that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage agent will cleave a nucleic acid molecule in response to the formation of cleavage structures; it is not necessary that the cleavage agent cleave the cleavage structure at any particular location within the cleavage structure.

The cleavage agent may include nuclease activity provided from a variety of sources including the CLEAVASE enzymes, the FEN-1 endonucleases (including RAD2 and XPG proteins), Taq DNA polymerase and E. coli DNA polymerase I. The cleavage agent may include enzymes having 5' nuclease activity (e.g., Taq DNA polymerase (DNAP), E. coli DNA polymerase I). The cleavage agent may also include modified DNA polymerases having 5' nuclease activity but lacking synthetic activity. Examples of cleavage agent suitable for use in the method and kits of the present invention are provided in U.S. Pat. Nos. 5,614,402; 5,795,763; 5,843,669; 6,090,606; 6,090,543; PCT Appln. Nos WO 98/23774; WO 02/070755A2; WO0190337A2; and WO 2003/073067, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage agent with an invasive cleavage structure (i.e., the treatment of a cleavage structure with a cleavage agent).

The term "target nucleic acid" and "target sequence," when used in reference to an invasive cleavage reaction, refers to a nucleic acid molecule containing a sequence that has at least partial complementarity with at least a first nucleic acid molecule (e.g. probe oligonucleotide) and may also have at least partial complementarity with a second nucleic acid molecule (e.g. INVADER oligonucleotide). The target nucleic acid is located within a target region and is identified by the fact that it as allows the successful formation of an invasive cleavage structure in combination with the first and second nucleic acid molecules that is cleavable by a cleavage agent.

The term "interfering sequence," when used in reference to an invasive cleavage reaction, refers to a nucleic acid molecule that has a similar or identical sequence to the "target sequence," which allows the formation of an invasive cleavage structure in combination with the first and second nucleic acid molecules that also form an invasive cleavage structure with the "target sequence." The interfering sequence is located within an interfering region the sequence of which is distinct from the target region in which the target sequence is located. For example, a 54 base "interfering sequence" is shown in FIG. 5 located within a larger interfering region (i.e. SEQ ID NO:2, which is in chromosome 18) with is identical to the 54 base "target sequence" shown in FIG. 5, which is located with a larger target region (i.e. SEQ ID NO:1, which is part of the TPMT gene located on chromosome 6).

The term "probe oligonucleotide," when used in reference to an invasive cleavage reaction, refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide— whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette," when used in reference to an invasive cleavage reaction, as used herein refers to an oligonucleotide or combination of oligonucleotides configured to generate a detectable signal in response to cleavage of a probe oligonucleotide in an INVADER assay. In preferred embodiments, the cassette hybridizes to an interfering cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides. The blocker oligonucleotides, as well as other sequences such as the first and second oligonucleotides (e.g. primary probe and INVADER oligo) may contain nucleotide analogs.

The term "sample," as used herein, is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid (e.g., blood or plasma), solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

DESCRIPTION OF THE FIGURES

FIG. 5 shows various sequences used in Example 1, including: i) the target region (SEQ ID NO:1) on chromosome 6 containing the 54 base TPMT target sequence (composed of the probe footprint and INVADER oligo footprint); ii) the interfering region (SEQ ID NO:2) on chromosome 18 containing the 54 base interfering sequence (composed of the probe footprint and the INVADER oligo footprint); an INVADER oligo (SEQ Id NO:6); Blocker 1 (SEQ ID NO:3); Blocker 2 (SEQ ID NO:4); Blocker 3 (SEQ ID NO:5), the portion of the INVADER oligo still available to hybridize in the presence of: blocker 1 (SEQ ID NO:7); portion of the INVADER oligo still available to hybridize in the presence of blocker 2 (SEQ ID NO:8); and the portion of the INVADER oligo still available to hybridize in the presence of blocker 3 (SEQ ID NO:9).

GENERAL DESCRIPTION OF THE INVENTION

Figure 1:
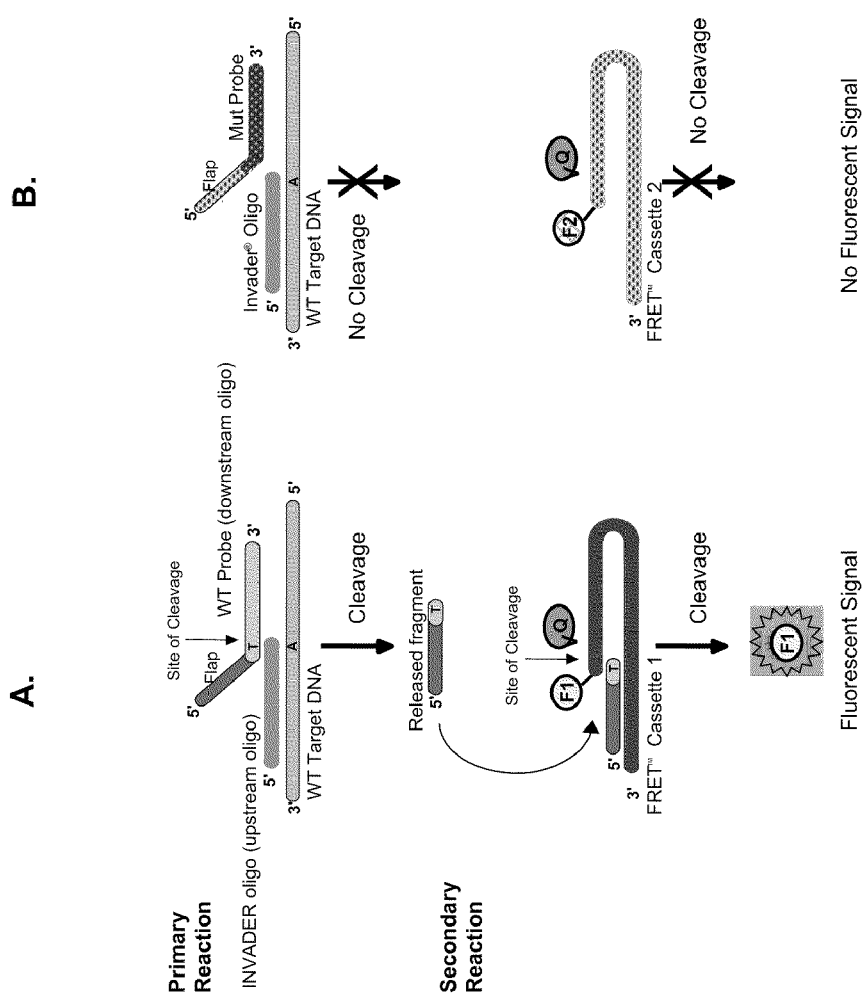
FIG. 1 shows a schematic diagram of INVADER oligonucleotides, probe oligonucleotides and FRET cassettes for detecting a wild-type single-nucleotide polymorphism.

The present invention provides methods, compositions, and kits for detecting the presence or absence of target sequences in a sample, where the sample also contains interfering sequences that are similar or identical to the target sequences (e.g. the target sequence is located in one part of a chromosome and the interfering sequence is located on another part of the same chromosome or on a different chromosome). In particular, the present invention provides blocker oligonucleotides that at least partially inhibit the formation of invasive cleavage structures with the interfering sequences but do not substantially inhibit the formation of invasive cleavage structures with the target sequences.

High sequence homology of irrelevant regions of a genome can interfere with a detection assays, such as the INVADER detection assay, by causing the hybridization of nucleic acid molecules (e.g. primary probe and INVADER oligonucleotides) to regions of the genome other than the targeted region of interest. The blocker oligonucleotides of the present invention take advantage of neighboring sequence dissimilarity. They are designed to block or inhibit binding to these locations and focus the second nucleic acid molecules (e.g. INVADER oligonucleotide) onto the targeted location. The present invention finds use with many different nucleic acid detection assays, particularly assays that use multiple hybridization oligonucleotides (e.g. ligase chain reaction, PCR, or other technologies).

Blocker oligonucleotides enable the interrogation of previously unavailable regions of the human genome (as well as sequences from other organisms). Alternatives to genotyping are more labor intensive and include approaches including capture and subsequent sequencing of messenger RNA, as well as primer-specific PCR pre-amplification of the desired region of the genome prior to interrogation with an INVADER assay or similar SNP detection assay. The present invention enables precise and specific interrogation of SNPs in the context of interfering sequences amongst the rest of the entire genome (e.g. human genome) and may be carried out, for example, in a single tube-single step reaction.

The blocker oligonucleotides of the present invention are, in preferred embodiments, employed with the INVADER SNP detection assay and applied to any analogous region of a human or animal genome. Additionally, the blocker oligonucleotides may be multiplexed in connection with a multiplexed INVADER assay designed to simultaneously interrogate several different locations. Additional embodiments include the use of the blocker oligonucleotides to improve the sensitivity and specificity of an INVADER genotyping assay that takes advantage of additional sequence unique to a given genotype that is adjacent to the targeted sequence of an INVADER genotyping assay. As an example, if an INVADER assay can detect genotype A with 10-fold greater sensitivity than it detects related genotype B on the basis of sequence similarities between the two, such "background" detection of genotype B may be reduced even further, or abolished completely, by the use of a blocker oligonucleotide that is designed to hybridize preferentially to genotype B and reduce or eliminate hybridization of the INVADER assay for genotype A to the analogous region in genotype A.

Example 1 describes the design and use of blocker oligonucleotides in the context of the TPMT*3B allele as there is a psudo-gene located on chromosome 18 that can interference with detection. FIG. 5 shows three blocker oligonucleotides that were designed (Blockers 1-3) that are able to hybridize to part of the INVADER oligonucleotide footprint (present on both the targeted TPMT sequence and chromosome 18) and also hybridize to sequence found on chromosome 18 (but not found in the TPMT gene). Blocker oligos similar to Blockers 1-3 may be generated by constructing similar sequences that are able to hybridize to both the INVADER footprint and the region adjacent to INVADER footprint that is only found on the interfering region (SEQ ID NO:2 on chromosome 18) and not on the target region (SEQ ID NO:1, part of the TPMT gene). Similar sequences that are generated may be tested by repeating the protocols in Example 1 with the candidate blocker oligos. Preferably blocker oligos have a higher Tm than the INVADER oligo, and cause the INVADER oligo, during a reaction, to have a Tm, with regard to the interfering sequence, that is lower than the temperature of reaction (e.g. 63° C.)—but will not significantly affect the Tm of the INVADER oligo with regard to target sequence. Software programs are available to calculate predicted Tm's in order to help design blocker oligonucleotides with such characteristics. This same design process for TPMT and its pseudo-gene can be used for other targeted sequences (e.g. in the human genome) that also show up elsewhere (e.g. also appear in the human genome). In this regard, blocker oligos for other targeted sequences that have interfering interfering sequences can be generated and used in an invasive cleavage assay, such as the INVADER assay. Additional details on the INVADER assay are provided below.

The present invention provides methods, compositions, and kits for forming a nucleic acid cleavage structure (preferably with blocker oligos) that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717; 5,985,557; 5,994,069; 6,001,567; 6,913,881; and 6,090,543, WO 97/27214, WO 98/42873, Lyamichev et al., Nat. Biotech., 17:292 (1999), Hall et al., PNAS, USA, 97:8272 (2000), each of which is herein incorporated by reference in their entirety for all purposes). The INVADER assay detects hybridization of probes to a target by enzymatic cleavage of specific structures by structure specific enzymes.

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In preferred embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the 'target' nucleotide sequence do not match perfectly at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

In the INVADER assays, the probes can turn over without temperature cycling to produce many signals per target (i.e., linear signal amplification). Similarly, each target-specific product can enable the cleavage of many FRET probes. The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties. In preferred embodiments, blocker oligonucleotides are employed with the INVADER assay.

In certain embodiments, the target nucleic acid sequences are amplified prior to detection (e.g. such that amplified products are generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197, 557, issued Mar. 6, 2001, and in PCT application WO 98/39485, each incorporated by reference herein in their entireties for all purposes.

In some embodiments, the present invention provides methods for detecting a target sequence, comprising: providing a) a sample containing DNA amplified by extension of 3' ends in nicked double-stranded genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequences and said oligonucleotides if said target sequences are present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive q 29 polymerase (as described, e.g., in U.S. Pat. Nos. 5,198,543 and 5,001,050, each herein incorporated by reference in their entireties for all purposes) in combination with exonuclease-resistant random primers, such as hexamers.

In some embodiments, the present invention provides methods for detecting a target sequence, comprising: providing a) a sample containing DNA amplified by extension of multiple primers on genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some preferred embodiments, said primers are random primers. In particularly preferred embodiments, said primers are exonuclease resistant. In other embodiments, one or both of the first and second oligonucleotide (e.g. primary probe and INVADER oligo) is configured to also serve as a PCR primer. In certain preferred embodiments, blocker oligos are included in the reaction. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

The present invention further provides assays in which the target nucleic acid is reused or recycled during multiple rounds of hybridization with oligonucleotide probes and cleavage of the probes without the need to use temperature cycling (e.g., for periodic denaturation of target nucleic acid strands) or nucleic acid synthesis (e.g., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (The kinetics of oligonucleotide replacement. Luis P. Reynaldo, Alexander V. Vologodskii, Bruce P. Neri and Victor I. Lyamichev. J. Mol. Biol. 97: 511-520 (2000)), multiple probes can hybridize to the same target, allowing multiple cleavages, and the generation of multiple cleavage products.

EXAMPLES

The following examples are provided in order to demonstrate and further illustrate certain preferred embodiments and aspects of the present invention and are not to be construed as limiting the scope thereof.

Example 1

INVADER Assays Employing Blocker Oligonucleotides

This example describes the use of the INVADER assay with and without various blocker oligonucleotides in order to detect polymorphisms in the thiopurine methyltransferase (TPMT) gene. An INVADER assay configured to detect the TPMT *3B (G460A) mutation was used in an attempt to detect this mutation. This INVADER assay was composed of the following sequences:

```
INVADER oligo-
                                         (SEQ ID NO: 6)
5' CATTTGCGATCACCTGGATTAATGGCAACTAATGA 3';

Wild-type Probe-
                                         (SEQ ID NO: 10)
5' ACGGACGCGGAGCTCCTCTATCCCAAATCAT -
hexanediol 3';

Mutant Probe-
                                         (SEQ ID NO: 11)
5' CGCGCCGAGGTTCCTCTATCCCAAATCATG - hexanediol 3';

FRET 10Fam/Z28-
            (X = Z28; Y = 6FAM; SEQ ID NO: 12)
5'- YTCTXAAGCCGGTTTTCCGGCTGAGACTCCGCG
TCCGT - hexanediol 3';

FRET 25 Red/Z28-
            (X = Z28; Y = Z35 (Red), SEQ ID NO: 13)
5' YTCTXAAGCCGGTTTTCCGGCTGAGACCTCGGCGCG -
hexanediol 3'.
```

Figure 2:
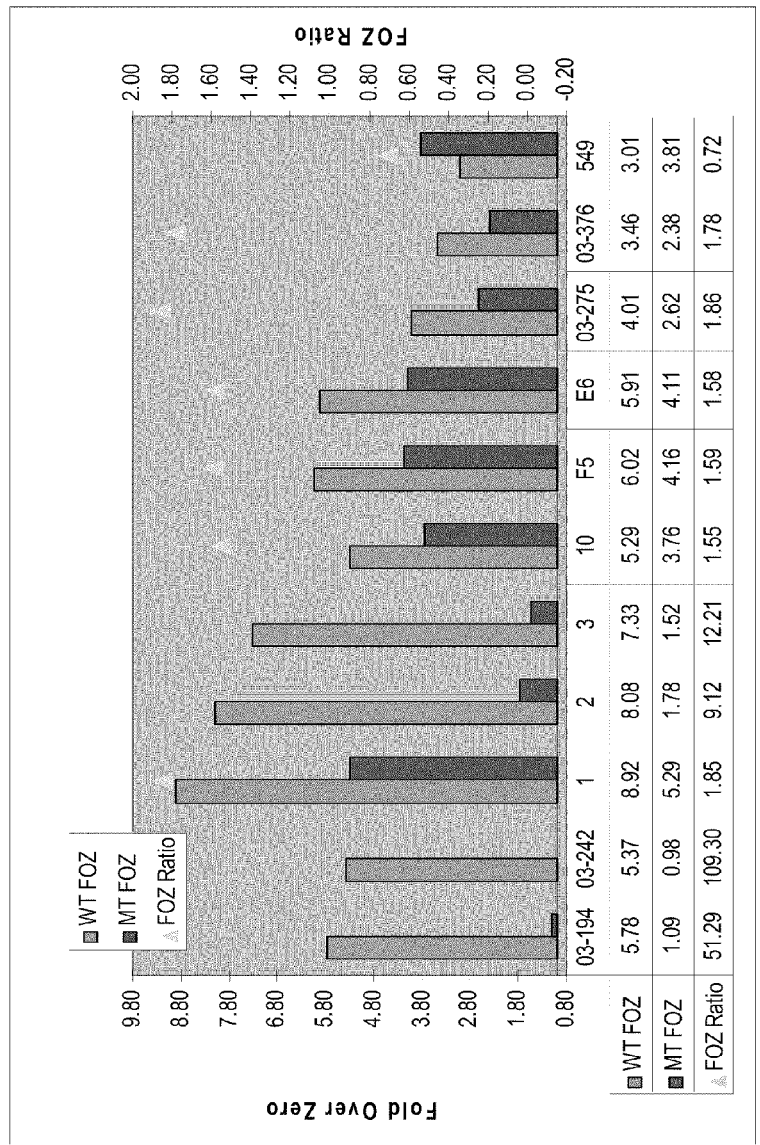
FIG. 2 shows the results, from Example 1, of detecting the TPMT *3B mutation and wild-type with the INVADER assay without blocker oligos on Genomic DNA.
Figure 3:
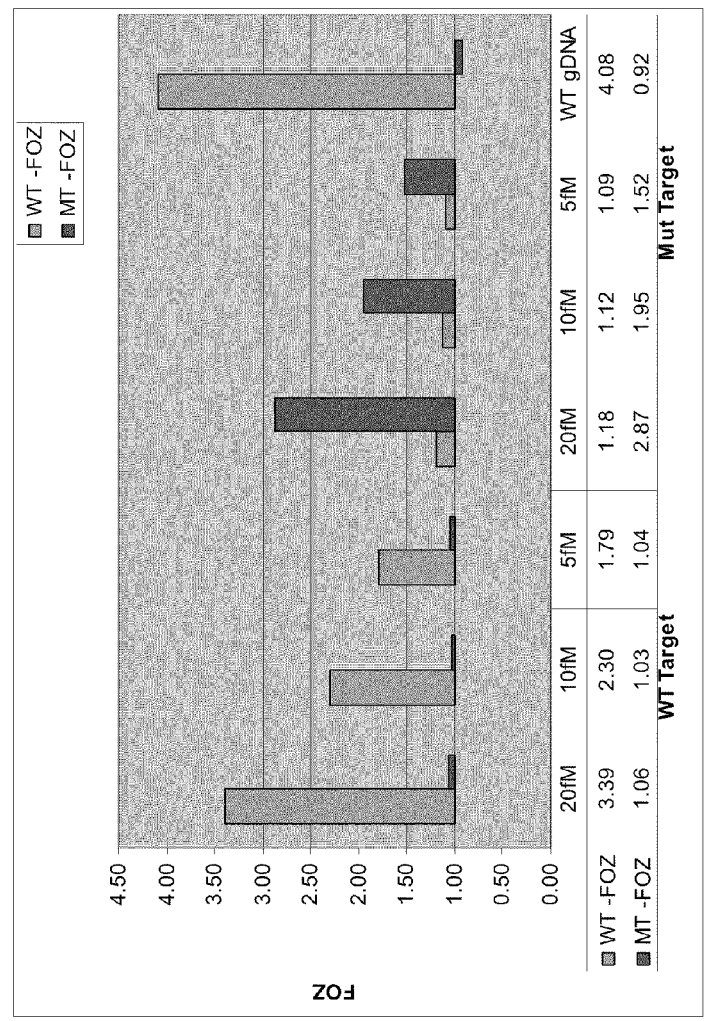
FIG. 3 shows the results, from Example 1, of detecting the TPMT *3B mutation and wild-type with the INVADER assay without blocker oligos on synthetic targets.
Figure 4:
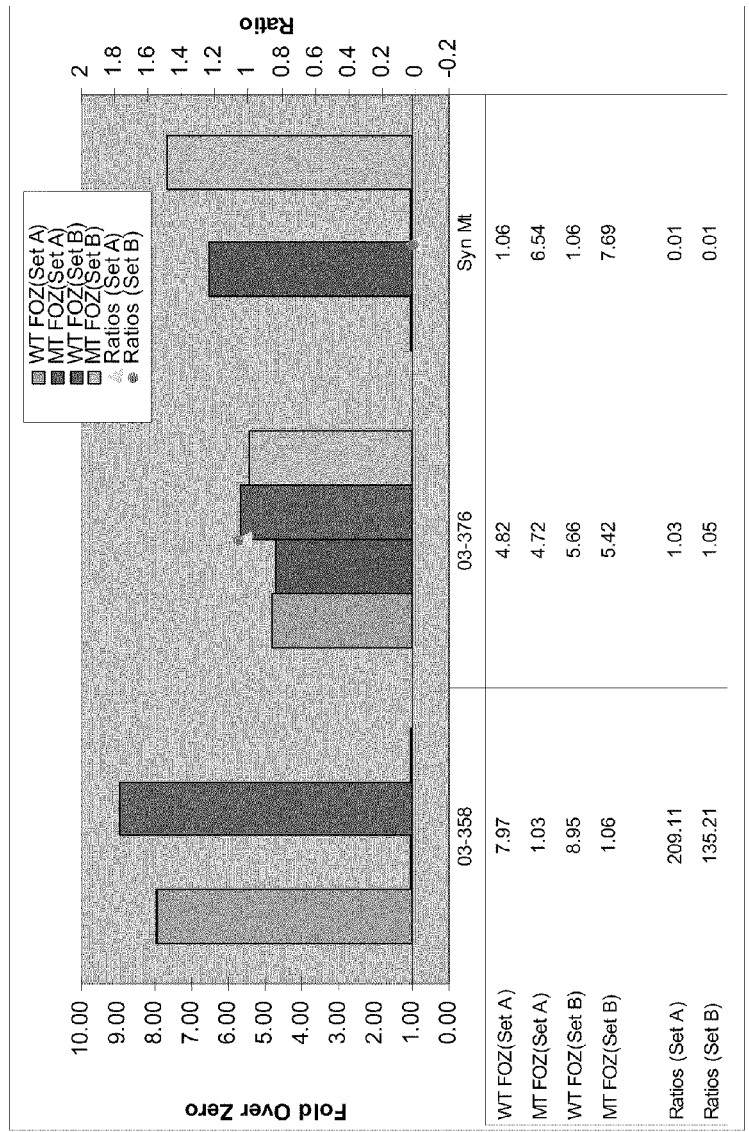
FIG. 4 shows the results, from Example 1, of detecting the TPMT *3B mutation and wild-type using PCR and the INVADER assay without blocker oligos.

The results of employing this INVADER assay yielded a higher than expected signal for the wild type (WT) allele. This result was most apparent on known heterozygous genomic DNA samples where the ratio of wild type to mutant signal (het ratio) averaged 1.70 rather than the expected ratio of 1.0 (see FIG. 2). The same assay generated het ratios close to the expected 1.0 (1.03 and 1.05) when run on PCR product generated from the same genomic DNA sample (see FIG. 4). Additionally, there is no significant difference in the performance with synthetic wild type and mutant targets (see FIG. 3). In addition, inflated wild type signal caused known homozygous mutant sample to be miscalled as heterozygous. One potential cause of the elevated wild type signal would be the presence of a second copy of the wild type sequence elsewhere in the genome. The results of sequence homology searches supported this assumption. BLAST and BLAT searches using GenBank (NCBI) and The Human Genome Browser at UCSC, revealed a TPMT processed pseudogene on chromosome 18, with significant homology to the TPMT gene located on chromosome 6 (see alignment in FIG. 5). This included a stretch of 60 bases with 100% homology that encompassed the 54 base INVADER assay oligonucleotide footprint (Probe+INVADER oligonucleotide) surrounding the *3B locus (see FIG. 5).

Blocker oligonucleotides were designed to prevent signal generation from the pseudogene on chromosome 18, but not the TPMT chromosome 6 (*3B). The designs take advantage of sequence differences between chromosomes 6 and 18 immediately adjacent to the 5' end of the INVADER oligonucleotide (see FIG. 5). In this Example, the Blocker oligonucleotide are fully complementary to the adjacent, non-homologous region of chromosome 18 and a portion of the 5' end of the Invader oligonucleotide. The Blocker oligonucleotides were also designed to not be fully homologous with chromosome 6. The Blocker therefore hybridizes with chromosome 18 and interferes with, or "blocks," the binding of the *3B INVADER oligonucleotide to the pseudogene, while it does not form a stable hybrid on chromosome 6 so that signal generation is not inhibited at the *3B locus.

Three Blocker oligonucleotides were designed that extend 29 bases to the 5' side of the INVADER sequence and extend 14, 17 or 26 bases into the 5' end of the Invader sequence. These three Blocker oligonucleotides, shown in FIG. 5, are designated as follows: Blocker 1 (974-Z5, SEQ ID NO:3), Blocker 2 (1319-Z1, SEQ ID NO:4), and Blocker 3 (1319-Z3, SEQ ID NO:5). The Blocker oligonucleotides were designed to have predicted Tms greater than that of the INVADER oligonucleotide (79, 80.8, and 82° C. versus 75° C. for the INVADER oligonucleotide) and thus will bind preferentially on chromosome 18. As shown in FIG. 5, the predicted Tm of the INVADER oligonucleotide after the 14 nucleotide displacement caused by blocker 1 (which leaves a only a portion of the INVADER oligonucleotide, SEQ ID NO:7, available for hybridizing) is 58.5° C.; the predicted Tm of the INVADER oligonucleotide after the 17 nucleotide displacement caused by blocker 2 (which leaves a only a portion of the INVADER oligonucleotide, SEQ ID NO:8, available for hybridizing) is 50.8° C.; the predicted Tm of the INVADER oligonucleotide after the 26 nucleotide displacement caused by blocker 3 (which leaves a only a portion of the INVADER oligonucleotide, SEQ ID NO:9, available for hybridizing) is 19° C. All three of these INVADER oligo Tm's (58.5° C., 50.8° C., and 19° C.) are lower than the 63° C. reaction temperature, and consequently the INVADER oligonucleotide will not form a stable hybrid with chromosome 18 in the presence of these blockers oligos. However in the chromosome 6 *3B sequence, 19 of the 29 Blocker nucleotides extending outside of the INVADER oligonucleotide are non-complementary (see FIG. 5). Therefore, the predicted Tm of the Blocker oligonucleotides on chromosome 6 is 31.4-54.4° C. for Blockers 1-3. The *3B INVADER oligonucleotide therefore binds preferentially to chromosome 6 in the presence of any one of these three blockers.

An INVADER assay for the TPMT gene utilizing the blocker oligos and INVADER assay sequences described above was set up as follows: INVADER reaction mixtures were prepared that contained 5 uL of DNA Reaction Buffer 1 (14% PEG, 40 mM MOPS (pH 7.5), 56 mM MgC12, 0.02% ProClin 300); 1 uL 1 uM each INVADER oligo plus Blocker oligo in TE, 1 uL 10 uM each WT and Mut probes in TE, 1 uL 5 uM FAM FRET in TE, 1 uL 5 uM Red FRET in TE, 1 uL 40 ng/uL Cleavase X in Cleavase dilution buffer. INVADER assays using this reaction mixture were performed as follows: 10 uL of volume containing sample DNA (or an appropriate control) was added to a reaction well and overlayed with 20 uL of mineral oil. The nucleic acids were denatured by incubation at 95° C. for 5 min, and the wells were then cooled to 63° C. 10 uL of the above INVADER reaction mixture (with one of the three blockers) was added, and mixed by pipetting. The reactions were incubated at 63° C. for 4 hours, cooled to 4° C., and scanned in a fluorescence microplate reader.

Figure 6:
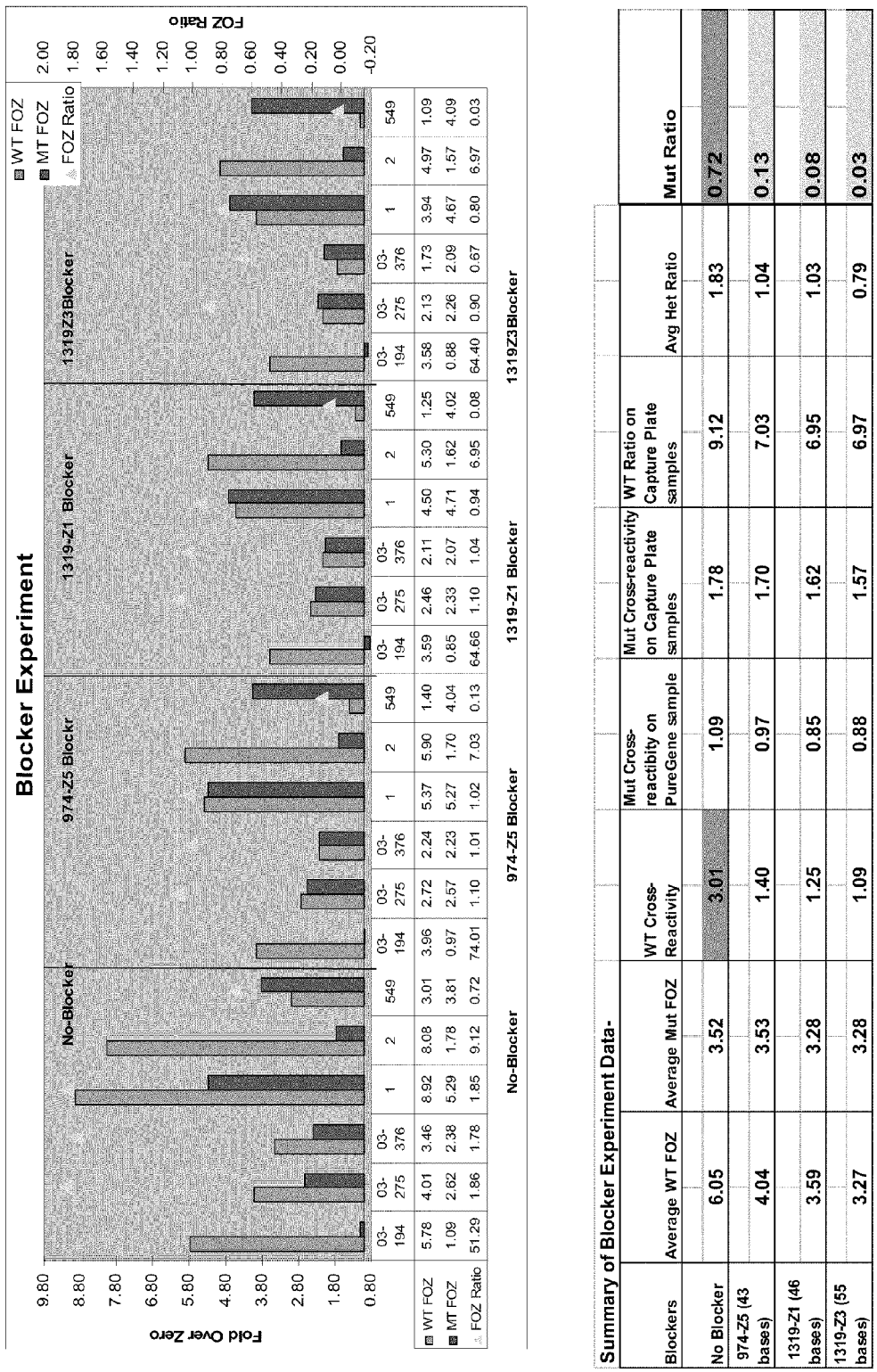
FIG. 6 shows the results, from Example 1, of detecting the TPMT *3B mutation and wild-type with the INVADER assay with Blocker oligo 1, Blocker oligo 2, and Blocker oligo 3.

Inclusion of Blockers in the reaction displaces INVADER oligonucleotides from chromosome 18 and allows normal detection of the *3B polymorphism on chromosome 6, such that heterozygote genomic samples have ratios close to 1.0 (see FIG. 6). More over, the homozygous mutant sample miscalled heterozygous by the non-blocker INVADER assay is now correctly detected as a mutant sample by the Blocker+ INVADER assay (FIG. 6). Mutant sample was called a het with ratio of 0.72 by INVADER without Blocker, whereas with Blocker in the assay, the mutant ratios are 0.13, 0.08 or 0.03 respectively. The final concentration of the blocker oligos is the same as the INVADER oligonucleotide (1 pmol). The two oligonucleotides are mixed in the same tube so that there is no change in the format.

Example 2

INVADER Assay Detection of TPMT *3C (A719G) and TPMT *2 (G238C)

This Example describes an INVADER assay configured for detecting TPMT *3C (A719G) and an INVADER assay configured for detecting TPMT *2 (G238C). These assays do not require the use of a blocker oligonucleotide. These assays may, for example, be used alone or in combination with each other or the TPMT *3B (G460A) described above in Example 1.

The TPMT *3C INVADER assay is composed of the following sequences:

```
INVADER oligo-
                                    (SEQ ID NO: 14)
5' AACATGTCAGTGTGATTTTATTTTATCTATGTCTCATTT
ACTTTTCTGTAAGTAGAA 3';

Wild-type probe-
                                    (SEQ ID NO: 15)
5' CGCGCCGAGGTATAACTTTTCAAAAAGACAG -
hexanediol 3';

Mutant probe-
                                    (SEQ ID NO: 16)
5' ATGACGTGGCAGACCATAACTTTTCAAAAAGACAGT -
hexanediol 3';

FRET 16 FAM/Z28-
               (X =Z28; Y =6FAM; SEQ ID NO: 17)
5' YTCTXAAGCCGGTTTTCCGGCTGAGACCTCGGCGCG -
hexanediol 3';
```

```
FRET 29 Red/Z28-
                    (X =Z28; Y =Z35 (Red); SEQ ID NO: 18)
5' YTCTXTTCGGCCTTTTGGCCGAGAGAGTCTGCCA
CGTCAT - hexanediol 3'.
```

This TPMT *3C INVADER assay may be used, for example, with the same conditions and reagents as described in Example 1 above in order to detected the A719G TPMT polymorphism. In certain preferred embodiments, the TPMT *3C and TPMT *3B INVADER assays are employed on the same sample to detect the TPMT*3A allele.

The TPMT *2 INVADER assay is composed of the following sequences:

```
INVADER oligo-
                                      (SEQ ID NO: 19)
5' CCTCTATTTAGTCATTTGAAAACATAATTTAAGTGTAAATGTATGAT
TTTATGCAGGTTT T 3';

Wild-type probe-
                                      (SEQ ID NO: 20)
5' AGCTCGTCCGACAGCAGACCGGGGAC - hexanediol 3';

Mutant probe-
                                      (SEQ ID NO: 21)
5' CGCGCCGAGGCCAGACCGGGGACAC - hexanediol 3';

FRET 16 FAM/Z28-
                    (X =Z28; Y =6FAM; SEQ ID NO: 17)
5' YTCTXAAGCCGGTTTTCCGGCTGAGACCTCGGCGCG -
hexanediol 3';

FRET 27 RED/Z28-
                    (X = Z28; Y = Z35 (Red); SEQ ID NO: 22)
5' YTCTXTTCGGCCTTTTGGCCGAGAGATGTCGGAC
GAGCT - hexanediol 3'.
```

This TPMT *2 INVADER assay may be used, for example, with the same conditions and reagents as described in Example 1 above in order to detected the G238C TPMT polymorphism.

All publications and patents mentioned in the above specification are herein incorporated by reference as if expressly set forth herein. Various modifications and variations of the described assays of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A composition, comprising:
   a) first and second nucleic acid molecules, wherein said first and second nucleic acid molecules are configured to form a first invasive cleavage structure with a target sequence within a target region, and wherein said first and second nucleic acid molecules are also able to form a second invasive cleavage structure with an interfering sequence within an interfering region, and
   b) blocker oligonucleotides configured to at least partially hybridize with said interfering sequence such that formation of said second invasive cleavage structure is at least partially inhibited.

2. The composition of claim 1, further comprising c) a cleavage agent, wherein said cleavage agent is capable of cleaving said first nucleic acid molecules when said first nucleic acid molecules form an invasive cleavage structure comprising said second nucleic acid molecules and said target sequence or said interfering sequence.

3. The composition of claim 1, further comprising said target region.

4. The composition of claim 3, further comprising said interfering region.

5. The composition of claim 1, wherein said first and second nucleic acid molecules and said blocker oligonucleotides are configured such that at least 70 percent of invasive cleavage structures formed in the presence of said target sequence and said interfering sequence are said first invasive cleavage structures.

6. The composition of claim 1, wherein the melting temperature of said blocker oligonucleotides when hybridized to said interfering sequence is greater than the melting temperature of said second nucleic acid molecules when hybridized to said interfering sequence.

7. The composition of claim 1, wherein said blocker oligonucleotides are configured to hybridize to at least a portion of said interfering sequence and to at least a portion of said interfering region that is not part of said interfering sequence.

8. The composition of claim 1, wherein said first nucleic acid molecules comprise a 5' portion and a 3' portion, wherein said 3' portion is configured to hybridize to said target sequence, and wherein said 5' portion is configured to not hybridize to said target sequence.

9. The composition of claim 1, wherein said second nucleic acid molecules comprise a 5' portion and a 3' portion, wherein said 5' portion is configured to hybridize to said target sequence, and wherein said 3' portion is configured to not hybridize to said target sequence.

10. The composition of claim 1, wherein said interfering sequence is identical to said target sequence.

11. The composition of claim 1, wherein said interfering sequence is at least 97 percent homologous to said target sequence.

12. The composition of claim 1, wherein said interfering sequence has five or fewer nucleotide base difference compared to said target sequence.

13. The composition of claim 1, wherein said target sequence and said interfering sequence are each at least 15 bases in length.

14. The composition of claim 1, wherein the Tm of said second oligonucleotide with regard to said interfering region less than 63° C.

15. The composition of claim 1, wherein said target region comprises a first gene, and wherein said interfering region comprises a first pseudo-gene.

16. The composition of claim 1, wherein said target sequence comprises a targeted polymorphic sequence.

17. The composition of claim 16, wherein said targeted polymorphic sequence is a single nucleotide polymorphism.

18. A composition for analyzing a target sequence, comprising:
   i) first and second nucleic acid molecules, wherein said first and second nucleic acid molecules are configured to form a first invasive cleavage structure with a target sequence, and wherein said first and second nucleic acid molecules are also able to form a second invasive cleavage structure with an interfering sequence;
   ii) a sample comprising: A) a target region suspected of containing said target sequence, and B) an interfering region comprising said interfering sequence;
   iii) a cleavage agent; and
   iv) blocker oligonucleotides configured to at least partially hybridize with said interfering region such that formation of said second invasive cleavage structure is at least partially inhibited.

* * * * *